United States Patent [19]

Lippard et al.

[11] Patent Number: 4,683,315
[45] Date of Patent: Jul. 28, 1987

[54] REDUCTIVE COUPLING OF LINEAR CARBON-CONTAINING LIGANDS VIA TRANSITION METAL COMPLEXES

[75] Inventors: Stephen J. Lippard; Patricia A. Bianconi, both of Cambridge, Mass.

[73] Assignee: Massachusetts Institute of Technology, Cambridge, Mass.

[21] Appl. No.: 761,399

[22] Filed: Aug. 1, 1985

[51] Int. Cl.$^4$ .............................................. C07F 9/00
[52] U.S. Cl. .................................... 556/12; 562/517; 562/523; 562/597; 534/14; 556/14; 556/15; 556/27; 556/28; 556/30; 556/31; 568/861
[58] Field of Search ................ 568/861; 562/517, 523, 562/597; 556/12, 14, 15, 16, 27, 28, 31

[56] References Cited

PUBLICATIONS

Uchiumi et al., J. Japan Petrol. Inst., vol. 25:4, pp. 197–204 (1982).
Farr et al., Organometallics, vol. 4:1, pp. 139–142 (1985).
Hoffmann et al., J. Am. Chem. Soc., vol. 105, p. 146 (1983).
Giandomenico et al., J. Am. Chem. Soc., vol. 104:5, pp. 1263–1271 (1982).
Cotton et al., J. Am. Chem. Soc., vol. 5, pp. 3734–3735 (1983).
Marks, Science, vol. 217:4564, pp. 989–997 (1982).
Barger, et al., J. Am. Chem. Soc., vol. 106:18, pp. 5178–5186 (1984).
Lentz, et al., Angew. Chem. Int. Ed. Engl., vol. 23:7, pp. 525–526 (1984).
Anderson, et al., J. Am. Chem. Soc., vol. 106:17, pp. 4743–4749 (1984).
Maj, et al., J. Am. Chem. Soc., vol. 104:15, pp. 4278–4280 (1982).
Berry et al., J. Am. Chem Soc., vol. 104:17, pp. 4712–4715 (1982).
McMurry, Acc. Chem. Res., vol. 16, pp. 411–417 (1983).
Cramer, et al., J. Am. Chem. Soc., vol. 105, pp. 6749–6750 (1983).
Burgmayer et al., Inorg. Chem., vol. 24:14, pp. 2224–2230 (1985).

*Primary Examiner*—Helen M. S. Sneed
*Attorney, Agent, or Firm*—George W. Neuner; Ernest V. Linek

[57] ABSTRACT

The present invention is directed to high-coordination transition metal complexes, i.e., those of coordination number seven and above, and the use thereof in the room temperature/atmospheric pressure formation of carbon-carbon bonds via reductive coupling of linear carbon-containing ligands, and methods for the isolation and recovery of the newly formed $C_2$ containing species.

9 Claims, No Drawings

REDUCTIVE COUPLING OF LINEAR CARBON-CONTAINING LIGANDS VIA TRANSITION METAL COMPLEXES

The Government has rights in this invention pursuant to Grant Number NSF CHE-8401426 awarded by the National Science Foundation.

BACKGROUND OF THE INVENTION

The present invention is directed to high-coordination transition metal complexes, i.e., those of coordination number seven and above, and the use thereof in the room temperature/atmospheric pressure formation of carbon-carbon bonds via reductive coupling of linear carbon-containing ligands, and methods for the isolation and recovery of the newly formed $C_2$ containing species.

The use of transition metals to catalyze the formation of new C—C bonds is an important part of industrial processes which use CO as a feedstock for products with more than one carbon atom. Commonly invoked mechanisms for metal catalyzed C—C bond making include carbonyl insertion (hydroformylation and methanol carbonylation) (see, Heck et al., *J. Am. Chem. Soc.*, 1961, 83, 4023; and Calderazzo, *Angew. Chem. Int. Ed. Engl.*, 1979, 17, 255), and polymerization of surface methylene (derived from CO and $H_2$) on metal surfaces to give linear hydrocarbons in Fischer-Tropsch synthesis (see, Fisher et al., *Brennst. Chem.*, 1926, 7, 97; *Chem. Ber.*, 1926, 59, 830; and Brady et al., *J. Am. Chem. Soc.*, 1980, 102, 6181; ibid, 1981, 103, 1287).

Other processes which effect C—C coupling include; (1) reductive elimination, Collman, et al., *Principles and Applications of Organotransition Metal Chemistry*, University Science Books, Mill Valley, CA, 1980, pp 234-245; (2) nucleophilic attack of carbanions at carbonyl, E. O. Fischer, *Adv. Organomet. Chem.*, 1976, 14, 1, or olefin, R. A. Holton, *J. Am. Chem. Soc.*, 1977, 99, 8083; (3) alkyl migration to carbonyl or carbene ligands; T. C. Flood, "Topics in Inorganic and Organometallic Stereochemistry", Eliel, et al., Wiley, New York, 1981, Vol. 12; Wojcicki, A. *Adv. Organomet. Chem.*, 1973, 11, 87, Calderazzo, F. *Angew Chem., Int. Ed. Engl.*, 1977, 16, 299; Threlkel, et al., *J. Am. Chem. Soc.*, 1981, 103, 2650; Hayes, et al., ibid, 1981, 103, 4648; (4) coupling of alkynes, J. P. Collman, *Acc. Chem. Res.*, 1968, 1, 136; McAllister, et al., *J. Am. Chem. Soc.*, 1977, 99, 1666, nitriles Cotton, et al., *J. Am. Chem. Soc.*, 1979, 101, 5094; de Boer, et al., *J. Am. Chem. Soc.*, 1979, 153, 53, P. T. Wolczanski, Ph.D. Thesis, California Institute of Technology, Pasadena, CA, 1981; isonitriles, Giandomenico, et al., *J. Am. Chem. Soc.*, 1982, 104, 1263; olefins, McDermit, et al., *J. Am. Chem. Soc.*, 1976, 98, 6529; Erker, et al., ibid, 1979, 101, 5451, and/or aldehydes, Manriquez, et al., *J. Am. Chem. Soc.*, 1978, 100, 2716, normally affording metallacyclic products; (5) addition of alkynes, McKinney, et al., *J. Am. Chem. Soc.*, 1981, 103, 5584, olefins, Tebbe, et al., *J. Am. Chem. Soc.*, 1978, 100, 3611; R. F., Schrock, *J. Am. Chem. Soc.*, 1980, 102, 3272, to metal carbenes, yielding four-membered metallacycles; (6) bimolecular carbene-carbene coupling to olefins, Fisher, et al., *Chem. Ber.*, 1974, 107, 3326; Schrock, et al., *J. Am. Chem. Soc.*, 1978, 100, 2389; Casey, et al., *J. Chem. Soc., Chem. Commun.*, 1975, 985, Ott, et al., *J. Am. Chem. Soc.*, 1981, 103, 5922, and the less extensively documented processes (7) olefin insertion into metal-alkyl bonds; P. L. Watson, *J. Am. Chem. Soc.*, 1982, 104, 337 and references therein; (8) carbene-carbonyl coupling to afford coordinated ketenes, Herrmann, et al., *Angew. Chem. Int. Ed. Engl.*, 1978, 17, 525; Redhouse, et al., ibid, 1976, 15, 615; Herrman, et al., *J. Am. Chem. Soc.*, 1979, 101, 3133; Wolczanski, et at., *Acc. Chem. Res.*, 1980, 13, 121. D. H. Berry et al., *J. Am. Chem. Soc.*, 1982, 104, 4712 reported a new type of carbon-carbon bond-forming reaction: the direct coupling of two carbonyl ligands of a binuclear transition-metal complex.

Compounds of the group 6 transition metals of the general formula $[M(CNR)_7]^{2+}$, $[M(CNR)_6X]^+$ (R=alkyl, X=Cl, Br, I, CN, $SnCl_3$; R=aryl, X=I), and $M(CNR)_5X_2$ comprise a well studied class; Giandomenico, et al., *Organometallics*, 1982, I, 142; Bonati, et al., *Inorg. Chem.*, 1970, 9, 2642; Lewis, et al., *Inorg. Chem.*, 1972, 11, 621; Novotny, et al., *J. Chem. Soc., Chem. Commun.*, 1973, 202; Lewis, et al., *J. Am. Chem. Soc.*, 1975, 97, 2697; Lam, et al., *Inorg. Chem.*, 1978, 17, 2127; Brant, et al., *J. Am. Chem. Soc.*, 1970, 101, 6588; Girolami, et al., *J. Organomet. Chem.*, 1979, 182, C43; LaRue, et al., *Inorg Chem.*, 1980, 19, 315; Mialki, et al., *J. Am. Chem. Soc.*, 1980, 102, 1095; Szalda, et al., *Inorg. Chem.*, 1981, 20, 3851. These complexs have close inter-ligand contacts which could give rise to ligand migration or coupling reactions. Reductive coupling of two isocyanide ligands was found to occur in the reaction of $[Mo(CN-t-C_4H_9)_6I]^+$ with zinc. Lam, et al., *J. Am. Chem. Soc.*, 1977, 99, 617. In particular, a brilliant red crystalline material was obtained, the nature of which was revealed by X-ray crystallography. The complex turned out to be $[Mo(CN-t-C_4H_9)_4(CHN-t-C_4H_9)_2I]I$, containing what is formally (N,N'-di-tert-butyldiamino)acetylene coordinated to molybdenum.

The Lam et al. chemistry was subsequently extended to the complexes $[Mo(CN-t-C_4H_9)_6X]^+$, wherein X=Cl and Br (Lam, C. T., Ph.D. Dissertation, Columbia University, New York, 1977). These gave the same type of product although the chloride and bromide complexes were obtained in lower yields and isolated as their tetrahalozincate(II) salts. The complex $[Mo(CN-t-C_4H_9)_6I]^+$ could be recovered from $[Mo(CN-t-C_4H_9)_4(CNH-t-C_4H_9)_2I]^+$ photochemically in the presence of free tert-butyl isocyanide. Corfield, et al., *Inorg. Chem.*, 1981, 20, 922. No organic products were isolated, however.

An attempt to couple reductively tert-butyl isocyanide ligands in $[Mo(CN-t-C_4H_9)_7]^{2+}$ gave rise to $[Mo(CN-t-C_4H_9)_4(CNH-t-C_4H_9)_2(CN)]^+$, in which both reductive coupling, (Lam, et al., *J. Am. Chem. Soc.*, 1977, 99, 617,) and dealkylation of the tert-butyl isocyanide ligands occurred. (Dewan, et al., *Inorg. Chem.*, 1981, 20, 4069.)

Giandomenico et al., in *J. Am. Chem. Soc.*, 1982, 104, 1263-1271 describe the synthesis of a variety of seven-coordinated molybdenum(II) and tungsten(II) complexes containing linear ligands, especially alkyl isocyanides. These complexes, when subjected to reductive coupling conditions, permit the coupling of two of the isocyanide ligands, with the formation of a C≡C bond. Recovery of the acetylene species by oxidation to the corresponding N,N-dialkyl oxamide was also reported.

Hoffmann et al., in *J. Am. Chem. Soc.*, 1983, 105, 146-147, describe a "Theoretical Prescription for Reductive Coupling of CO or CNR Ligands" via transition metal complexes. It should be noted that the authors specifically state that the concept espoused is theoretical. The penultimate paragraph (p 147) reads as follows, "We look forward to experimental realization of this new reaction type."

However, Farr et al., in *Organometallics,* 1985, 4, 139-142, describe the synthesis and reactions of seven-coordinate technetium and rhenium complexes containing linear alkyl isocyanide ligands, and state that "attempts to couple the coordinated alkyl isocyanide ligands in the seven-coordinate technetium(III) and rhenium(III) complexes to produce coordinated (RNHC≡CNHR) species, by analogy to known Mo(II) and W(II) chemistry, yielded only reductive elimination to form $(M(CNR)_6)^+$ cations." That is, by following the chemistry described in Giandomenico et al., supra, Farr et al. were unable to achieve reductive coupling. Failure to achieve reductive coupling of carbon monoxide using the techniques set forth by Hoffmann et al., supra, was also reported recently by Templeton et al., *Inorg. Chem.,* 1985, 24, 2224-2230.

The present invention is directed to complexes and methods which achieve such a reductive coupling between linear carbon-containing ligands, particularly, carbon monoxide.

SUMMARY OF THE INVENTION

The present invention is directed to high-coordination transition metal complexes, i.e., those of coordination number seven and above, which permit the room temperature/atmospheric pressure formation of carbon-carbon bonds via reductive coupling and permit the isolation of the newly formed $C_2$ containing species. As used herein the term "isolation" means the recovery of the $C_2$ containing species, free from association with the transition metal complex.

More particularly, the present invention is directed to high-coordination transition metal complexes, containing an early transition metal, e.g., V, Nb, Ta; Cr, Mo, W; Mn, Tc, or Re, and a linear carbon-containing ligand, e.g., C≡O, and the like.

The invention is also directed to methods of using the transition metal complexes of the present invention for the reductive coupling of linear carbon-containing ligands, to isolable intermediates formed in the methods of the invention, and to methods of isolating the coupled species.

In a preferred embodiment, two carbon monoxide molecules, bound as linear ligands to an early transition metal complex, especially niobium or tantalum, are allowed to react in the presence of a reducing agent, such as magnesium dust, with a second transition metal complex, forming an isocarbonyl-containing complex, i.e., a species wherein the C≡O ligands are bound to the two transition metals. Treatment of the isocarbonyl-containing complex with a silyl species affords an early transition metal complex containing two $R_3SiO—C≡$ species, which are reductively coupled forming an acetylene bond there between. The resulting product is a coordinated disiloxyacetylene ($R_3SiO—C≡C—OSiR_3$).

Release of the new carbon-carbon bonded species from the transition metal complex may be accomplished via several routes, each affording a desirable end product. For example, reduction of the metal-disiloxyacetylene complex with hydrogen affords ethylene glycol, a compound used in the production of polyester. Alternatively, oxidation of the metal-disiloxyacetylene complex with an oxidizing agent such as hydrogen peroxide affords oxalic acid, an intermediate for numerous compounds. Another application for the complex is in the conversion of synthesis gas (syngas) to higher hydrocarbons, specifically ethylene glycol and derivatives thereof, with the concomitant regeneration of the complex, i.e., a catalytic system.

DETAILED DESCRIPTION OF THE PREFERRED EMBODIMENTS

The present invention is directed to transition metal complexes of the formula 1:

wherein;

M is an early transition metal selected from the group consisting of vanadium, niobium, tantalum, chromium, molybdenum, tungsten, manganese, technetium, and rhenium;

$Y_1$ and $Y_2$ are each independently selected from linear carbon-containing ligands, particularly C≡O, CNR, NCR, C≡CR, CN, C≡S, $CO_2$, $CS_2$, and the like, wherein R is hydrogen or an alkyl chain or aryl group as defined herein, with the exception that $Y_1$ and $Y_2$ are not both CNR;

$L_1$, $L_2$, $L_3$, and $L_4$, are each independently selected from groups of ligands that are 2-electron donors, including phosphines, amines, arsines, sulfides, and the like, and wherein, for example, two or more of $L_1$, $L_2$, $L_3$, and/or $L_4$, can be combined as a bidentate or multidentate ligand; and X is halogen or pseudohalogen such as F, Cl, Br, I, CN, NCS, and the like.

A particularly preferred transition metal complex useful in the reductive coupling reaction of the present invention is represented by the formula 3:

As used herein, the term alkyl includes carbon groups having straight, branched or cyclic configurations. The term encompasses saturated or unsaturated species of up to about 30 carbon atoms. Preferably, the alkyl group is a straight chain, saturated moiety, of up to about 20, more preferably up to about 12 carbon atoms. Groups such as these are readily accessable to the skilled chemist using ordinary synthetic methodology.

As used herein, the term aryl, includes all ring compounds exhibiting the characteristic "aromatic" NMR downfield resonance (i.e., >7 ppm) for protons bound to the ring. Examples of such "aromatic" ring compounds include, benzene and substituted benzenes, anthracenes, naphthalenes, and the like, heteroaromatic molecules such as pyridine, and the like.

As used herein, the term "2-electron donor ligands" means those ligands which contain an atom, generally having a lone pair of electrons, said atom being capable of contributing two electrons to the d-orbital of the transition metal with which they complex. Such ligands are readily determinable by artisans skilled in the field of coordination chemistry, and/or transition metal organometallic chemistry. For example, these ligands include substituted phosphines, amines, arsines, and sulfides.

The following reaction scheme (I) sets forth one general process for the reductive coupling reaction between two carbon monoxide ligands ($Y_1$ and $Y_2$), and illustrates the preferred starting materials, isolable intermediates, and products of one embodiment of the present invention. Similar processes can be set forth for the reductive coupling of other carbon-containing linear ligands in accord with the teachings of the present invention.

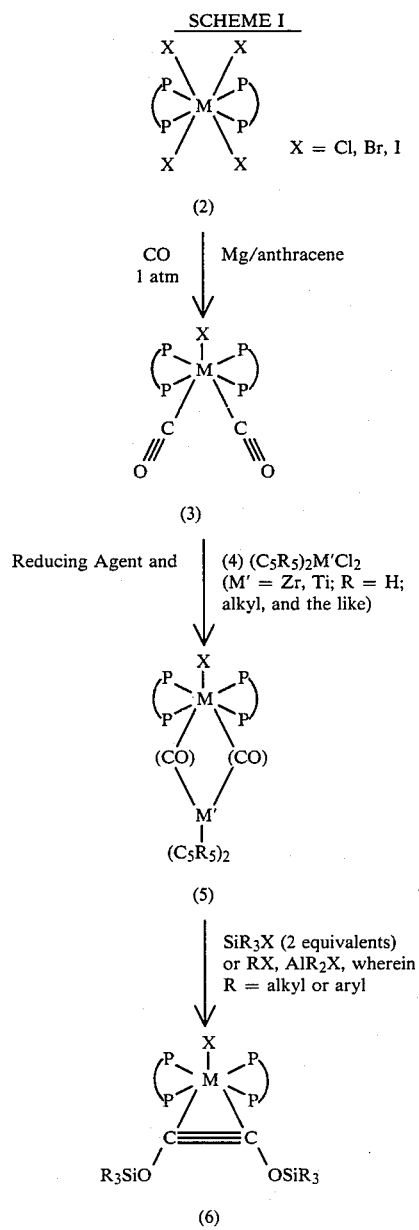

A. Reduction:

Compound (6) is reduced with $H_2$, Lithium Aluminum Hydride, other hydrides, and like reducing agents to afford:

$$HOCH_2-CH_2OH \quad (7)$$
and derivatives thereof

B. Oxidation:

Compound (6) is oxidized with oxidizing agents such

-continued
SCHEME I as hydrogen peroxide, other peracids, and the like to afford:

$$HOOC-COOH \quad (8)$$
and derivatives thereof, such as
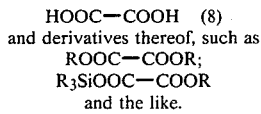
and the like.

C. Catalytic:

Compound (6) is reduced as above, with the generation of a product such as ethylene glycol and the regeneration of compound (3).

As illustrated in Scheme I, the eight-coordinate early transition metal species (2), which contains for example, phosphine ligands such as dmpe, a bidentate ligand (1,2-bis(dimethylphosphino)ethane), and four halide ligands, is first allowed to react with a reducing agent such as Mg, Na, or the like, and CO at one atmosphere to afford the seven-coordinate complex (3).

Reaction of the seven-coordinate complex with a second metal compound (4), such as the bis(pentamethyl cyclopentadienyl)zirconium dichloride illustrated, in the presence of a reducing agent such as magnesium metal, magnesium anthracene, or sodium/potassium alloy, affords an isolable isocarbonyl species, such as (5)—wherein the carbon monoxide ligands are bound to both the early transition metal and the zirconium.

Treatment of the isocarbonyl species with at least two equivalents of a Lewis acid, such as an alkyl silyl halide, e.g., trimethylsilyl chloride, affords the seven-coordinate early transition metal complex (6)—wherein the two carbon monoxide ligands are bound together via an acetylene linkage.

Isolation of the newly formed $C\equiv C$ containing species can be effected by (a) reducing; or (b) oxidizing conditions, depending upon the desired end-products. As illustrated in Scheme 1, these various conditions afford the products; ethylene glycol; oxalic acid, and related compounds.

For example, reducing [Ta(dmpe)$_2$(Me$_3$SiOC$\equiv$COSiMe$_3$)X], wherein X is either Cl, or SiMe$_3$, is accomplished using hydrogen in a pressurized bomb at up to about 1000 atmospheres, or by reaction with an alkali metal hydride. Preferably, the pressure is in the range of from about 10 atm. to about 400 atm. The reaction can be heated to assist in the formation of the desired products, which in this case are ethylene glycol and [Ta(dmpe)$_2$(H)$_2$X]. Ethylene glycol is collected and purified by distillation.

Another method for the isolation of useful products from the transition metal complex involves an oxidation reaction. In this case, the complex, for example, [Ta(dmpe)$_2$(Me$_3$SiCO$\equiv$COSiMe$_3$)X], wherein X is either Cl, or SiMe$_3$, is allowed to react with, for example, hydrogen peroxide or a similar peracid, or Ag$^+$, preferably under an inert atmosphere. The mixture is filtered to remove the Ta(V) oxides, and an organic solvent such as toluene is added until precipitation ceases. The precipitated oxalic acid is purified by recrystallization, such as from water/benzene.

A preferred use of the complex of the present invention is the catalytic preparation of new $C_2$ containing species, and the isolation thereof with regeneration of structure 3. For example, the complex [Ta(dmpe)$_2$(Me$_3$SiOC$\equiv$COSiMe$_3$)X], wherein X is Cl or SiMe$_3$, is formed via reactions starting with the compound [Ta(dmpe)$_2$(CO)$_2$Cl]. Reaction of the acetylene complex with syngas (CO/H$_2$, 1:1), at a pressure of from about 1 to 500 atmospheres, preferably from about 10 to 300 atmospheres, with stirring and heating, affords the desired product, ethylene glycol, and regeneration of [Ta(dmpe)$_2$(CO)$_2$X]. With the regeneration of the catalyst, the process can be repeated.

The present invention will be further illustrated by the following examples which are intended to aid in the understanding thereof, but are not to be construed as limitations thereof.

All reactions and manipulations were performed in dried glassware under an inert atmosphere using either standard Schlenk techniques or a nitrogen-filled glovebox. Solvents were distilled from standard drying agents under N$_2$. Bis(dimethylphosphino)ethane(dmpe), [(C$_5$H$_5$)$_2$TiCl$_2$] (Cp$_2$TiCl$_2$), [(C$_5$Me$_5$)$_2$TiCl$_2$] (Cp'$_2$TiCl$_2$) and [(C$_5$Me$_5$)$_2$ZrCl$_2$)] (Cp'$_2$ZrCl$_2$) were purchased from Strem and used as received. SiMe$_3$Cl was degassed under a stream of nitrogen and stored over molecular sieves in a drybox.

EXAMPLE 1

Preparation of (Ta(Me$_3$SiOC≡COSiMe$_3$)(dmpe)$_2$Cl) (1) and (Ta(Me$_3$SiOC≡COSiMe$_3$)(dmpe)$_2$(SiMe$_3$)) (2)

Mg powder (approximately 1 g, 41 mmol) and I$_2$ (50–80 mg, 0.20–0.32 mmol) are stirred and heated in 20 ml THF until the mixture is colorless (approximately 5 min.). Ta(CO)$_2$(dmpe)$_2$Cl (0.573 g, 1.00 mmol) and Cp'$_2$ZrCl$_2$ (0.432 g, 1.00 mmol) are added along with another 20 ml of THF.

The reaction mixture is stirred until red-brown, or until the CO bands of the starting material in the IR (1810, 1740 cm$^{-1}$) have vanished and the bands characteristic of isocarbonyl (1720, 1600 cm$^{-1}$) have grown in.

This transformation may take from 3 to 24 hr; the formation of isocarbonyl is accelerated if the mixture is kept slightly above room temperature.

When the CO bands in the IR of the starting material have completely vanished, the mixture is filtered and the residual Mg is washed with THF, typically 20 ml. The combined extracts are cooled to −78° and SiMe$_3$Cl (0.254 ml, 2.00 mmol) is added. This reaction is allowed to warm to room temperature and stirred 12 hr. The solvent is then removed in vacuo and the solid green residue is extracted with 80 ml pentane.

The extract is filtered, the volume of the filtrate is reduced to about 4 ml and cooled to −30°. Green crystals slowly deposit over 2–12 hr. These crystals have been shown by X-ray crystallography, $^1$H, $^{13}$C, and $^{31}$P NMR to be a mixture of title compounds (1) (about 70%) and (2) (about 30%). If more than two equivalents of SiMe$_3$Cl are used in this procedure, the ratio of compounds (1) to (2) changes to about 1:1.

EXAMPLE 2

Using the procedure of Example 1 with Cp$_2$TiCl$_2$ (0.249 g, 1.00 mmol) in place of Cp'$_2$ZrCl$_2$ results in the formation of approximately a 1:1 mixture of compounds (1) and (2).

EXAMPLE 3

Using the procedure of Example 1 with Cp'$_2$TiCl$_2$ (0.389 g, 1.00 mmol) in place of Cp'$_2$ZrCl$_2$ results in the formation of approximately a 30%:70% mixture of compounds (1) and (2). If more than two equivalents of SiMe$_3$Cl are used, the ratio of compound (1) to compound (2) changes to about 20% to 80%.

EXAMPLE 4

Mg powder (about 1 g) and anthracene (10 mg) are stirred in 20 ml of THF and 40 μl of EtBr is added. After 24 h stirring, Ta(CO)$_2$(dmpe)$_2$Cl (0.500 g, 0.873 mmol) and Cp$_2$TiCl$_2$ (0.217 g, 0.873 mmol) or Cp'$_2$ZrCl$_2$ (0.377 g, 0.873 mmol) are added. After three hours the red-brown solutions show no starting material carbonyl bands in the IR. Isocarbonyl bands (1720, 1600 cm$^{-1}$) are present. Addition of SiMe$_3$Cl and workup as in Example 1 results in the formation of compound (1) at approximately 5%, compound (2) at approximately 5%, and [Ta(dmpe)$_2$(SiMe$_3$OC≡COSiMe$_3$)Br], at about 90%.

EXAMPLE 5

Using the procedure of Example 1 with HgCl$_2$ (0.136 g, 0.5 mmol) in place of I$_2$ results in the formation of approximately a 90%:10% mixture of compounds (1) and (2). Using a larger amount of HgCl$_2$ (1.08 g, 4.0 mmol) in this procedure results in the formation of compound (1) only.

This invention has been described in detail including the preferred embodiments thereof. However, it will be appreciated that those skilled in the art, upon consideration of this disclosure, may make modifications within the spirit and scope of this invention as set forth in claims appended hereto.

What is claimed is:

1. A process for the formation of an isolable C$_2$ containing compound comprising the steps:
   (a) reacting an early transition metal seven coordinate complex of the formula:

(1)

wherein;
M is an early transition metal selected from the group consisting of vanadium, niobium, tantalum, chromium, molybdenum, tungsten, manganese, technetium, and rhenium;
Y$_1$ and Y$_2$ are each independently selected from the group of linear carbon-containing ligands consisting of C≡O, CNR, NCR, —C≡CR, CN, C=S, CO$_2$ and CS$_2$, wherein R is hydrogen, an alkyl group, or an aryl group, with the exception that Y$_1$ and Y$_2$ are not both CNR;
L$_1$, L$_2$, L$_3$, and L$_4$, are each independently selected from ligands that are 2-electron donors;
X is halogen or pseudohalogen;
with a second metal complex of the formula:

M'X$_2$L$_1$'L$_2$' wherein:
M' is a Lewis Acid selected from the group consisting of Ti, Zr, Hg, Al, Zn, Mg, and Na;
L$_1$' and L$_2$' are ligands selected from the group consisting of cyclic hydrocarbons which ensure a cis orientation of Y$_1$ and Y$_2$ groups upon reaction with Formula I above;

in the presence of a sufficient quantity of a reducing agent selected to effect the formation of a complex wherein $Y_1$ and $Y_2$ are bound to both M and M'; and (b) reacting the species formed in step (a) with a sufficient quantity of a Lewis Acid such that an isolable species is formed, said species containing a new $C_2$ bond between the $Y_1$ and $Y_2$ carbon atoms bound to M.

2. The process of claim 1, further comprising (c) isolating said new $C_2$ containing species formed in step (b).

3. The process of claim 2, wherein reductive conditions are employed in the isolation.

4. The process of claim 3, wherein the reductive conditions comprise treatment of the complex formed in step (c) with hydrogen gas, syngas, or hydride reducing agents.

5. The process of claim 4, wherein the isolated $C_2$ containing compound is ethylene glycol or derivatives thereof.

6. The process of claim 2, wherein oxidizing conditions are employed in the isolation.

7. The process of claim 6, wherein the oxidizing conditions comprise treatment of the complex formed in step (c) with hydrogen peroxide, $Ag^+$, or a similar oxidizing agent.

8. The process of claim 6, wherein the isolated $C_2$ containing compound is oxalic acid or dialkyl, diaryl, disilyl or mixed esters thereof.

9. A catalytic process for the formation of a carbon-carbon bond comprising the steps:

(a) reacting a transition metal complex having the formula:

(I)

with $L_5L_6M'X_2$ in the presence of a reducing agent to form the complex:

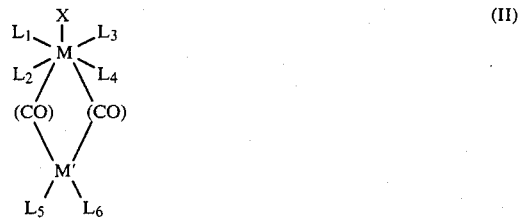

(II)

wherein;

M is an early transition metal selected from the group consisting of vanadium, niobium, tantalum, chromium, molybdenum, tungsten, manganese, technetium, and rhenium;

$L_1$, $L_2$, $L_3$, and $L_4$, are each independently selected from ligands that are 2-electron donors;

X is halogen or pseudohalogen;

M' is a Lewis Acid selected from the group consisting of Ti, Zr, Hf, Al; and $L_5$ and $L_6$ are ligands selected from the group consisting of cyclic hydrocarbons which ensure a cis orientation of the CO groups upon reaction with Formula I above;

(b) treating the resulting compound (II) of step (a) with a Lewis Acid (LA—X), thereby forming the compound:

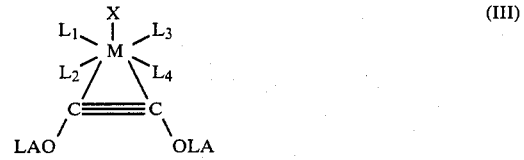

(III)

and regenerating the compound $L_5L_6M'X_2$; and (c) treating the resulting compound (III) of step (b) with an admixture of CO and $H_2$, thereby forming ethylene glycol or derivatives thereof, with the concomitant regeneration of compound (I).

* * * * *